United States Patent [19]
Scott et al.

[11] Patent Number: 5,470,825
[45] Date of Patent: * Nov. 28, 1995

[54] BASOPHIL GRANULE PROTEINS

[75] Inventors: Randy W. Scott, Sunnyvale, Calif.;
Gerald J. Gleich, Rochester, Minn.;
Craig G. Wilde, Foster City, Calif.

[73] Assignee: Incyte Pharmaceuticals, Inc., Palo Alto, Calif.

[*] Notice: The portion of the term of this patent subsequent to Jul. 10, 2010, has been disclaimed.

[21] Appl. No.: 259,564

[22] Filed: Jun. 15, 1994

Related U.S. Application Data

[63] Continuation of Ser. No. 551,263, Jul. 10, 1990, abandoned.
[51] Int. Cl.$^6$ .............................. A61K 38/02; C07K 2/00
[52] U.S. Cl. ................. 514/2; 530/300; 530/350
[58] Field of Search ....................... 530/350, 351, 530/300; 514/2

[56] References Cited

U.S. PATENT DOCUMENTS 4,935,370  6/1990  Franke ........................ 435/252.33

OTHER PUBLICATIONS

Denburg et al., "Partial Separation and Functional Characterization of Guinea Pig Basophil–Stimulating Factor," *Int. Arch. Allergy Appl. Immunol.* (1986) 79(3):312–319.
Wasmoen et al, "Biochemical and Amino Acid Sequence Analysis of Human Eosinophil Granule Major Basic Protein," *J. Biol. Chem.* (1988) 263:12559–12561.
Geysen et al., "Use of Peptide Synthesis to Probe Viral Antigens for Epitopes to a Resolution of a Single Amino Acid," *Proc. Natl. Acad. Sci. (USA)* (1984) 81:3998–4002.
Stockinger et al. (1990) Blood 75:1820–1826.
Denburg et al. (1986) Biological Abstracts 81:Abst. 100863.
Dvorak et al. (1977) J. Immunology 119:38–46.
Ackerman et al. (1983) J. Exp. Med. 158:946–961.
Dvorak et al. (1989) Lab. Investigations 60:557–567.
Wasmoen et al. (1981) Proc. Nat. Acad. Sci., USA, 263: 12559–12561.
Blom et al. (1993) Scand. J. Immunol. 37:203–208.
Weller et al. (1984) J. Biol. Chem. 259: 15100–15105.
Abu–Ghazaleh (1992) J. Leucocyte Biol. 52:611–618.
Ackerman et al. (1993) J. Immunol. 150:465–468.
Durack et al. (1981) Proc. Nat. Acad. Sci., USA, 78:5165–5169.
Denburg et al. (1985) Blood 66:312–318.
Galli et al., *Prog. Allergy* (1984) 34:1–142.
Brown et al., *J. Immunol.* (1982) 129:790–796.
Ogilvie et al., *Immunol.* (1980) 39:385–389.
Juhlin et al., *Lancet* (1977) 1:1233–1235.
Schwartz et al., *Immunological Diseases*, Samter et al. (eds.), Little Brown & Co. 4th ed., pp. 157–201 (1988).
Solley et al., *J. Clin. Invest.* (1976) 58:408–420.
Charlesworth et al., *J. Clin. Invest.* (1989) 83:1519–1526.
Dvorak et al., *J. Immunol.* (1974) 113:1694–1702.
Orenstein et al., *J. Immunol.* (1978) 121:586–592.
Ackerman et al., *J. Exp. Med.* (1982) 155:1597–1609.
Castells et al., *J. Immunol.* (1987) 138:2184–2189.
Newball et al., *J. Clin. Invest.* (1979) 64:466–475.

*Primary Examiner*—Robert A. Wax
*Assistant Examiner*—Gabriele E. Bugaisky
*Attorney, Agent, or Firm*—Carol L. Francis; Karl Bozicevic; Fish & Richardson

[57] ABSTRACT

Several natural polypeptides (basophil granule proteins, "BGP") derived from the cytoplasmic granules of human basophils, and modified forms thereof, are described. These polypeptides, the DNA which encodes them and antibodies which recognize them, are useful as diagnostics for, and treatments for, pathologies involving inflammatory and IgE-mediated responses, parasitic and helminthic infections, hypersensitivity reactions and certain types of leukocytic leukemias.

2 Claims, 1 Drawing Sheet

BASOPHIL GRANULE PROTEINS

This is a continuation of application Ser. No. 07/551,263, filed Jul. 10, 1990, now abandoned.

TECHNICAL FIELD

This invention is related to therapeutics and human immunology. More specifically, it relates to proteins found in the cytoplasmic granules of human basophils, to the genes which encode them, to the antibodies which recognize them, and to the use of these proteins, oligonucleotides, and antibodies in the diagnosis and treatment of disease.

BACKGROUND ART

The basophil, along with the mast cell, contains cytoplasmic granules with an affinity for basic dyes. The basophil is produced by the bone marrow and circulates in the blood. Basophils are associated with helminthic parasitic infections and allergic reactions and they possess a high affinity receptor for IgE antibodies. Little is known however about the proteins which comprise the granule, in part because, under normal conditions, basophils constitute less than 1% of peripheral blood cells and it is therefore difficult to obtain an adequate amount of purified material for study.

While some researchers have proposed that basophils are the precursors of mast cells, recent data suggests that basophils represent-terminally differentiated leukocytes, possibly more closely related to eosinophils (Galli, S. J. and Lichtenstein, L. M., in *Allergy:Principles and Practice*, Middleton et al (Eds.), 3rd Ed, Vol. 1 (1988), pp 106–134).

Basophils appear to participate in many inflammatory, immunological and pathological reactions. For a general review see Galli et al, *Prog Allergy* (1984) 34:1. The most striking tissue infiltrates of basophils occur in cutaneous basophil hypersensitivity reactions (Galli and Askenase, in *The Reticuloendothelial System:A Comprehensive Treatise*, Abramoff et al (Eds.) pg 321, Plenum Press 1986). Recent studies suggest that basophils are essential for expression of immunity to the feeding of larval *Amblyomma americanum* ticks. Here, basophils may collaborate with eosinophils in the expression of immunity by acting to attract eosinophils into tissues where the eosinophils subsequently release toxic cationic proteins (Brown, S. J. et al, *J Immunol* (1982) 129:790). Basophils are also elevated during helminthic infections, suggesting that they might participate in host defense to these parasites (Ogilvie, B. M. et al, *Immunol* (1980) 39:385; Lindor, L. J., *Parasite Immunol* (1983) 4:13; Juhlin, L. and Michaelsson, G., Lancet (1977) 1:1233). Evidence also exists that basophils function in hypersensitivity reaction (Schwartz, L. B. and Austen, K. F. in *Immunological Diseases*, Samter et al (Eds) Little Brown & Co 4th Ed, pg 157 (1988); Mitchell, E. B. *Clin Rev Allergy* (1983) 1:427), and in IgE mediated cutaneous late phase reactions (Solley, G. O. et al, *J Clin Invest* (1976) 58:408; Charlesworth, E. N. et al, *J Clin Invest* (1989) 83:1519).

Studies of human basophil granule proteins have been limited by the difficulty of-obtaining sufficient numbers of basophils because they constitute only about 0.5% of the total leukocyte population. Prior studies of proteins isolated from the basophils of guinea pigs repeatedly immunized with sheep blood revealed a mixture of neutral esterases-proteases and both trypsin and chymotrypsin-like serine hydrolases, Dvorak, H. F. et al, *J Immunol* (1974) 113:1699; *J Immunol* (1977) 119:38. Studies of the glycosaminoglycans (GAG) of these proteins showed a mixture of GAGs including chondroitin sulfate, dermatin sulfate, and small amounts of heparin sulfate (Orenstein, N. S. et al, *J Immunol* (1978) 121:586).

Several proteins have been localized to the human basophil granule including the eosinophil major basic protein (Ackerman, S. J. et al, *J Exp Med* (1983) 158:946) and the Charcot-Leyden crystal protein (Ackerman, S. J. et al, *J Exp Med* (1982) 155:1597). In addition, mast cell tryptase can be identified in human basophils at about 40 pg/cell, a level roughly 500-fold lower than in human mast cells (Casteils, M. C. et al, *J Immunol* (1987) 138:2184). In addition, bradykinin generating activity has been ascribed to basophils by virtue of the release of this enzyme from peripheral white blood cells by IgE dependent stimulation (Newball, H. H. et al, *J Clin Invest* (1979) 64:466).

The present invention was facilitated by a patient that presented with basophilic leukemia. Leukocyte counts were over $10^5$ cell/µl and contained 78% basophils. On two occasions this patient underwent cytophoresis for removal of leukocytes and a total of $1.5 \times 10^{11}$ basophils were obtained. Examination of the granule proteins of these basophils have revealed seven novel proteins with unique N-terminal amino acid sequences.

DISCLOSURE OF THE INVENTION

Several newly identified polypeptides (basophil granule proteins, "BGPs") are described which constitute some of the proteins found in the cytoplasmic granules of human basophils. These polypeptides, the DNA which encodes them and antibodies which recognize them, are critical for diagnostics for, and treatments for, pathologies involving inflammatory and IgE-mediated responses, parasitic and helminthic infections, hypersensitivity reactions and certain types of leukocytic leukemias.

One aspect of the invention is directed to BGPs, which include proteins found in the granules of basophils, and fragments, mutations and modifications of these natural proteins which retain their respective BGP biological characteristics. The polypeptides can be recombinantly produced by cells in culture or they can be isolated and purified from basophils.

Other aspects of the invention are an expression system comprising DNAs which encode these BGPs; host cells transformed with these expression systems; and methods to produce BGPs which utilize host cells transformed with said expression systems.

Still other aspects include antibodies, both monoclonal and polyclonal, which are specific for BGPs.

Additional aspects include methods of diagnosis and treatment of diseases characterized by abnormal expression or release of BGPs by basophils or other cells, or by genetic abnormalities within genes encoding BGPs, by application of the antibodies proteins and DNA probes described herein.

MODES OF CARRYING OUT THE INVENTION

Figure 1:
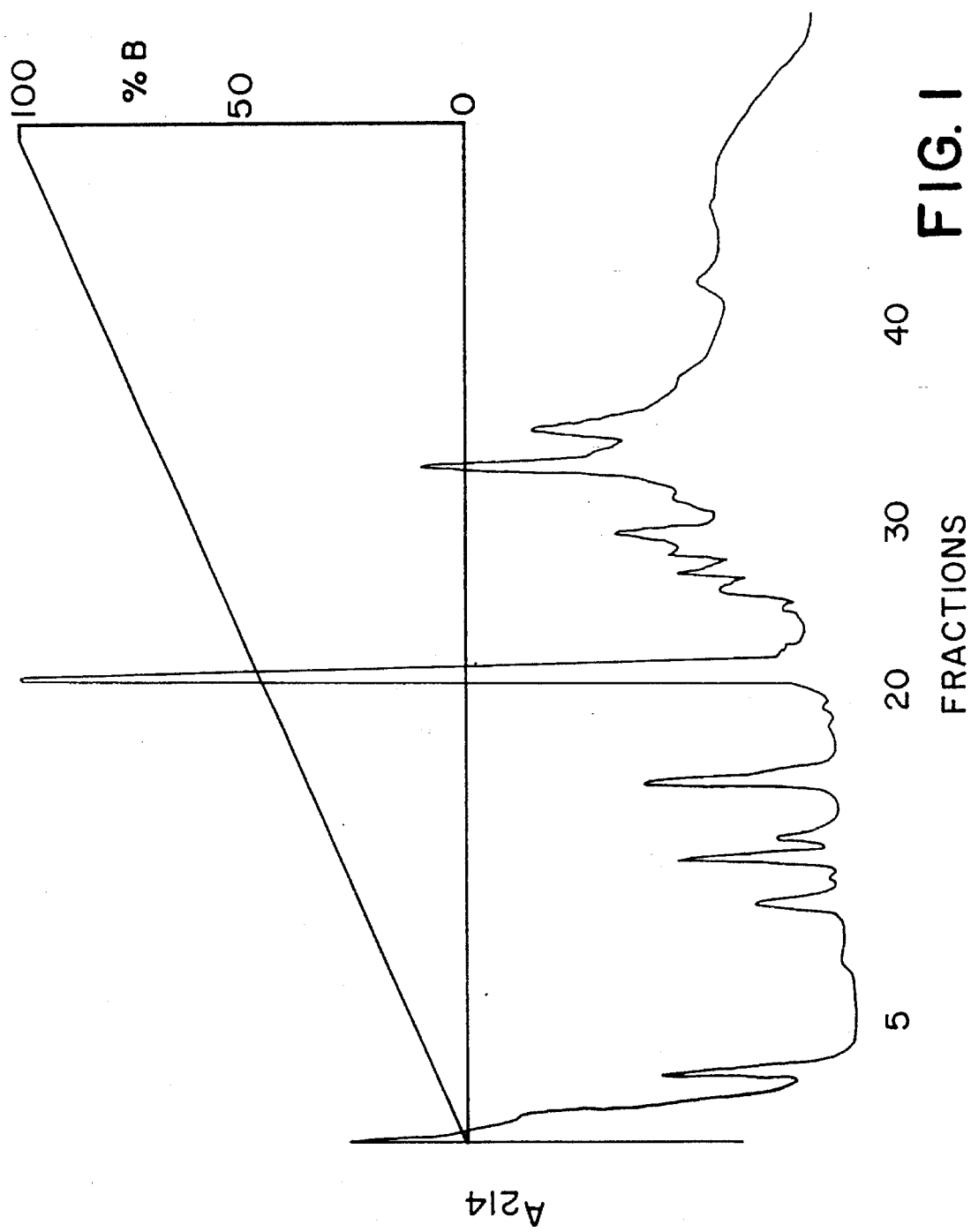
FIG. 1 shows a HPLC chromatogram of human basophil granule proteins.

As used herein, "basophil granule protein" or "BGP" refers to any of the seven novel proteins isolated from the cytoplasmic granules of human basophils as described herein, and to fragments, substitutions, mutations and modifications thereof which retain the biological characteristics of the natural BPG. The seven above-mentioned BGPs are thus a subset of all the polypeptides isolatable from human basophils.

A "mutated" protein is a protein with an altered primary structure (relative to the commonly occurring protein) resulting from changes in the nucleotide sequence of the DNA which encodes it. These mutations include allelic variants. A "modified" protein differs from the commonly occurring protein as a result of post-translational events which change the glycosylation or lipodation pattern, or the primary, secondary, or tertiary structure of the protein. Changes in the primary structure of a protein can also result from deletions, additions or substitutions. A "deletion" is defined as a polypeptide in which one or more internal amino acid residues are absent. An "addition" is defined as a polypeptide which has one or more additional internal amino acid residues as compared to the wild type. A "substitution" results from the replacement of one or more amino acid residues by other residues. A protein "fragment" is a polypeptide consisting of a primary amino acid sequence which is identical to a portion of the primary sequence of the protein to which the polypeptide is related.

Preferred altered forms of "natural" BPG described above are those which have at least 80% homology with natural BGP. At least 90% homology is more preferred, especially those including conservative substitutions.

Homology is calculated by standard methods which involve aligning two sequences to be compared so that maximum matching occurs; and then calculating the percentage of matches. The altered forms of natural BGP include those wherein one or more of the residues of the native sequence is deleted, substituted for, or inserted by a different amino acid or acids.

Preferred substitutions are those which are conservative, i.e., wherein a residue is replaced by another of the same general type. As is well understood, naturally occurring amino acids can be subclassified as acidic, basic, neutral and polar, or neutral and nonpolar. Furthermore, three of the encoded amino acids are aromatic. It is generally preferred that peptides differing from the natural BGP contain substitutions which are from the same group as that of the amino acid replaced. Thus, in general, the basic amino acids Lys, Arg, and His are interchangeable; the acidic amino acids aspartic and glutamic are interchangeable; the neutral polar amino acids Ser, Thr, Cys, Gln, and Asn are interchangeable; the nonpolar aliphatic acids Gly, Ala, Val, Ile, and Leu are conservative with respect to each other (but because of size, Gly and Ala are more closely related and Val, Ile and Leu are more closely related), and the aromatic amino acids Phe, Trp, and Thr are interchangeable. While proline is a nonpolar neutral amino acid, it presents difficulties because of its effects on conformation, and substitutions by or for proline are not preferred, except when the same or similar conformational results can be obtained. Polar amino acids which represent conservative charge include Ser, Thr, Gln, Asn; and to a lesser extent, Met. In addition, although classified in different categories, Ala, Gly, and Ser seem to be interchangeable, and Cys additionally fits into this group, or may be classified with the polar neutral amino acids. Some substitutions by amino acids from different classes may also be useful to produce altered BGP.

It should further be noted that if the BGP is made synthetically, substitutions by amino acids which are not encoded by the gene may also be made. Alternative residues include, for example, the omega amino acids of the formula $N_2N(CH_2)_n COOH$ wherein n is 2–6. These are neutral, nonpolar amino acids, as are sarcosine (Sar, t-butyl alanine (t-BuA), t-butyl glycine (t-BuG), N-methyl Ile (N-MeIle), and norleucine (Nle). Phenyl glycine, for example, can be substituted for Trp, Tyr, or Phe an aromatic neutral amino acid; citrulline (Cit) and metnionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be retained if one or more of these is substituted by hydroxyproline (Hyp).

It should be further noted that if the BGP is produced recombinantly as an intracellular protein, an N-terminal methionine residue may be retained in the finished product. Cleavage of the N-terminal methionine to liberate the native sequence may or may not be complete.

The biological "characteristics" of a protein refer to the structural or biochemical function of the protein in the normal biological processes of the organism in which the protein naturally occurs. Examples of biological characteristics of a BGP include its specific antigenicity or immunogenicity, its anti-helminthic activity when this is associated with a particular protein, and/or its ability to mediate inflammatory and immunological responses in vivo.

A host cell "expresses" a gene or DNA when the gene or DNA is transcribed. A protein or polypeptide is "expressed" when the protein or polypeptide has been produced.

"Recombinant host cell" means a procaryotic or eucaryotic cell which contains an expression vector comprising heterologous structural DNA and is capable of expressing the polypeptides encoded by the heterologous DNA.

A. Isolation of Basophil Granules

Clinical hematology laboratories are monitored to identify patients with chronic myelogenous leukemias with greater than $2-3 \times 10^4$ leukocytes/μl of blood and 10– 20% basophils. The basophils are purified by centrifugation over a cushion of Ficoll-Hypaque from which 95% are recovered from the interface with greater than 90% purity.

Purified basophils are lysed using modifications of the procedures described by Dvorak et al, *J Immunol* (1977) 119:38 (supra), for purification of guinea pig basophil granule proteins. Briefly, and in a typical and illustrative procedure, purified basophils are washed with PBS and contaminating erythrocytes are lysed by exposure to Tris-ammonium chloride for 5 minutes. The cell suspension is centrifuged at about 400 g, washed with Hank's BSA-EDTA and suspended in cold 0.25M sucrose containing DNAase and heparin using a volume of 15 ml for $8 \times 10^8$ basophils. The cell suspension is next centrifuged at 400 g for 10 minutes and the sediment is again suspended in 0.25M sucrose containing 2 mg DNAase per 15ml cell suspension. After 1–2 minutes, heparin (20 IU) dissolved in 2 ml 0.24M sucrose is added and the preparation is subjected to a shearing force by repeated passage (15 times) through a 20 gauge needle. The suspension is centrifuged at 400 g to remove any remaining intact cells, and the granules are then purified by centrifugation through a cushion of 40% sucrose. Finally, the proteins of the isolated basophil granules are solubilized by exposure to 0.05M borate buffer at pH 9 in the presence of 5 mM diisopropylfluorophosphate, $1 \times 10^{-7}$M pepstatin A, and 10 mM EDTA to inhibit protease activity.

B. Protein Fractionation and Sequencing

FIG. 1 is an HPLC chromatogram analysis of basophil granule extracts. Basophil granules were solubilized in 0.05M borate buffer, pH 9, and separated by reverse phase HPLC using a Brownlee BU-300 C4 column. The mobil phase was 0.1% trifluoroacetic acid (TFA) containing 0–70% acetonitrile. The percent B (0.1% TFA and 70% acetonitrile) is indicated on the graph shown in FIG. 1. The fractions are indicated on the abscissa. The ordinate shows adsorbance at 214 nm. Procedures involved in obtaining the chromatogram shown in FIG. 1 are described in further detail below.

The solubilized proteins of human basophilic granules, in the same solvent described supra, are separated by reverse phase HPLC using a Brownlee BU-300 C4 column. The mobile phase is 0.1% trifluoroacetic acid (TFA) containing 0–70% acetonitrile. Fractions are collected across the acetonitrile gradient as shown in FIG. 1, where absorbance at 214 nm is shown on the ordinate. The relative homogeneity of each fraction is determined by SDS-PAGE electrophoresis.

Although reverse phase HPLC is an extremely powerful technique, not all human basophil granule proteins can be purified by this technique alone. Thus, size exclusion chromatography can also be employed as a preliminary fractionation (e.g. Bio Sel TSK 125 in 50 mM borate pH 9.0) prior to HPLC.

If additional purification of size exclusion chromatography fractions is necessary prior to HPLC, ion exchange chromatography can also be employed. A Mono-O column (Pharmacia) is used under conditions as would be understood in the art whereby most typical proteins would bind to the column (e.g. 20 mM Tris, pH8.0). The proteins are then eluted in a gradient from 0 to 2 M NaCl.

Purified proteins recovered from reverse phase HPLC are sequenced by subjecting up to 100 pmoles (estimated from chromatographic peak height and staining intensity on acrylamide gels) to automated Edman degradation utilizing the Applied Biosystems 477A pulsed liquid phase protein sequenator.

For some granule proteins N-terminal sequencing may not be adequate to support efforts to clone the cDNAs. For instance, some granule proteins may be blocked or modified at the N-terminal or alternatively, the N-terminal sequences may not show favorable regions for generation of oligonucleotide probes. Such proteins are digested with trypsin and the tryptic peptides are purified in order to generate additional sequence information. The protein is concentrated to a 5 μl volume by vacuum centrifugation, and is then digested by incubation (4 hours, 37° C.) with 1/40 (w:w) TPCK-trypsin in 1 ml of 50 mM ammonium bicarbonate, pH 8.0. Tryptic fragments are purified for sequencing by reverse phase HPLC using a Brownlee RP 18 narrow bore column and an Applied Biosystems 130A liquid chromatograph—designed specifically for purification of pmole samples.

Sequence data thus obtained are compared to known protein sequences by computerized searches of the Protein Identification Resource of the NBRF, and of the Swiss protein database, in order to determine their novelty or relationship to other protein sequences.

C. Screening of cDNA Libraries and the Molecular Cloning of Unique Basophil Granular Protein Encoding DNA Basophils mature in cultures of human umbilical cord blood cells. Thus these cultures can be used to prepare a cDNA library which is then screened for particular DNA sequences that encode proteins unique to human basophil granules (BGP) (Saito, H. et al, *Proc Nat Acad Sci* (1988) 85:2288). Other candidate cDNA libraries include unstimulated HL-60 cells, which may express BGPs, or HL-60 cells driven to basophilic differentiation by culturing in a protein free medium (Muroi, K. et al, *Leukemia Res* (1989) 13:157). Although basophils and mast cells appear to be distinct in their lineages, granules of both cells contain mast cell tryptase (Castells, M. C. et al, *J Immunol* (1987) 138:2184) and these cells may therefore share other common proteins. Therefore cDNA libraries made from human mast cells (e.g. HMC-1) are another source of BGP encoding sequences. The preparation of these cDNA libraries is described in detail in Maniatis, T. et al, *Molecular Cloning*, (1982) CSHL Press, and is well known to those skilled in the art. A convenient approach is the insertion of cDNA fragments into a lambda phage vector e.g. lambda gt10 or lambda gt11 as described by Maniatis, supra.

Methods of screening cDNA libraries are also well known to those skilled in the art. The amino acid sequence of the BGPs is analyzed utilizing programs from DNAstar (Madison Wis.) in order to identify optimal regions for construction of oligonucleotide probes. Redundant oligonucleotide probes are synthesized with a DNA synthesizer (380A: Applied Biosystems Inc. Foster City Calif.) by the phosphoramidite method. Oligonucleotides are purified on Sephadex G-50 columns and stored at −20° C. The redundant probes are 5'-labeled with τ-[$^{32}$P]ATP (E.I. du Pont de Nemours & Co., Inc., Boston, Mass.) using T4 polynucleotide kinase. Libraries are screened using up to $10^6$ individual plaques per library, with the redundant oligonucleotide probes. Duplicate nylon membranes containing phage are prepared and prehybridized in 5× SSPE (0.9M NaCl, 50 mM $NH_2PO_4$, 5 mM EDTA, pH7.4), 0.2% SDS, and 0.005% denatured salmon sperm DNA for 2 hours at 50° C. with 8 filters per 50 ml prehybridization fluid per bag. Membranes are hybridized with approximately 1 ng of labeled probe per ml, in fresh hybridization fluid, overnight at the appropriate temperature for the redundant probe mixture. Membranes are then washed at room temperature for 45 minutes in 1 liter of 5× SSPE per 40 filters, followed by a 1 minute wash in fresh buffer at 50° C., slightly air-dried, and exposed to Kodak XAR-5 film, with intensifying screens, for 72 hours at −70° C.

After analysis, filters are stripped of hybridized label by incubation in 5× SSPE at 70° C. for 10 minutes and subsequently hybridized with a second probe under the same conditions. This procedure is repeated for each probe. Recombinant clones which hybridize with probes will be selected from the library and plaque purified.

Recombinant phage DNA is then purified and digested with an appropriate restriction endonuclease to yield the amplified cDNA insert. Inserts are then ligated into M13mp series phage and sequenced using the dideoxy method described by Sanger (Biggin, M. D. et al, *Proc Nat Acad Sci* (1983) 80:3963). Depending on the size of the cDNA, it may be necessary to restrict the clone, and subclone the fragments into M13. If the cDNA clones are not complete, a repeat screen of the library with the partial cDNA would be required. The complete sequence of the BGP cDNA is then compared against known sequences in the GenBank database. DNAstar is used for nucleotide and polypeptide analyses and sequence comparisons.

Selected cDNA inserts which encode a BGP can then be incorporated into an expression system. The cDNA is operably linked to heterologous control sequences to form an expression vector. The control sequences are chosen to be functionally compatible with the recombinant host cell into which the expression vector is introduced. These procedures are known to those skilled in the art and described in Maniatis, supra.

Expression can be in procaryotic or eucaryotic systems. Procaryotes most frequently are represented by various strains of *E. coli*. However, other microbial strains may also be used, such as bacilli (e.g. *Bacillus subtilis*), various species of *Pseudomonas,* or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al., Gene (1977) 2:95. commonly used procaryotic control sequences, which are defined herein to include operons with promoters for transcriptional initiation, optionally with an operator, along with ribosome binding site sequences, include such commonly used promoters as the beta-lactamase (penicillinase) promoter, lactose (lac) promoter systems (Chang et al., *Nature* (1977) 198:1056), the tryptophan (trp) promoter system (Goeddel et al., *Nucleic Acids Res* (1980) 8:4057), the lambda-derived PL promoter and N-gene ribosome binding site (Shimatake et al., *Nature* (1981) 292:128). Any available promoter system compatible with procaryotes can be used.

The expression systems useful in eucaryotic hosts comprise promoters derived from appropriate eucaryotic genes. A class of promoters useful in yeast, for example, includes promoters for synthesis of glycolytic enzymes, including those for 3-phosphoglycerate kinase (Hitzeman et al., *J Biol Chem* (1980) 255:207). Other promoters include those from the enolase gene (Holland, M. J., et al. *J Biol Chem* (1981) 256:1385) or the Leu2 gene obtained from YEp13 (Broach,, J., et al., *Gene* (1978) 8:121).

Suitable mammalian promoters include metallothionein, the early and late promoters from SV40 (Fiers et al., *Nature* (1978) 273:113), or other viral promoters such as those derived from polyoma, adenovirus II, bovine papilloma virus or retroviruses. Suitable viral and mammalian enhancers may also be used. In the event plant cells are used as an expression system, the nopaline synthesis promoter is appropriate (Depicker, A., et al., *J Mol Appl Gen* (1982) 1:561).

The expression system is constructed from the foregoing control elements which are operably linked to the BGP sequences by employing standard ligation and restriction techniques which are well understood in the art. Isolated plasmids, DNA sequences, or synthesized oligonucleotides are cleaved, tailored, and religated in the forms desired.

D. Analysis of the Genomic Sequence of BGP DNA

BGP-encoding genes are obtained from the genomic library of human fetal liver DNA in Charon 4A phage (ATCC 37333). The library contains $10^6$ independent recombinants with an insert size of 15–20 kb and it is screened with cDNA essentially as previously described. Phage are sequentially adsorbed onto duplicate 8×8 cm nylon membrane filters. Filters are prehybridized in 5× SSPE, 50% formamide, 5× Denhardt's solution, 0.5% SDS and 0.005% denatured salmon sperm DNA for 2 hours at 42° C. with 8 filters per 50 ml of prehybridization fluid. Filters are hybridized with approximately 1.0 ng of labeled basophil protein cDNA per ml of fresh prehybridization fluid, containing 10% dextran sulphate and 2x Denhardt's solution, overnight at 42° C. BGP cDNA is labeled with $\alpha^{32}P$ dCTP and purified by Sephadex G-50 chromatography. Filters are then washed twice at room temperature for 15 minutes in 1 liter 2× SSPE and 0.2% SDS per 40 filters, followed by two 15 minute 50° C. washes in 0.1× SSPE and 0.2% SDS, slightly air-dried, and exposed to Kodak XAR-5 film, with intensifying screens, for 48 hours at –70° C.

Positive clones are selected from the library and plaque purified. Various probes derived from the cDNA are utilized to determine whether or not a complete copy of the gene is contained within the genomic clone. Recombinant phage DNA is next extracted, purified, and subjected to restriction digestion—all processes which are well known to those skilled in the art. Southern blots of the restriction fragments are hybridized with BGP cDNA to identify fragments containing the BGP gene. These fragments are then isolated and sequenced. From this information a restriction map is constructed and the introns of the gene are identified.

E. Preparation Of Antibodies to BGPs

Two approaches are utilized to raise antibodies to BGP and both approaches can be used to generate either polyclonal or monoclonal antibodies. In one approach, as denatured protein from the reverse phase HPLC separation is obtained in quantities up to 75 µg, this denatured protein can be used to immunize mice using standard protocols; about 25 µg is adequate for immunization. For screening hybridomas, the denatured protein, which is soluble in 0.1% TFA and acetonitrile, can be radioiodinated and used to screen murine B-cell hybridomas for those which produce antibody. This procedure requires only small quantities of protein such that 20µg would be sufficient for labeling and screening of several thousand clones.

In the second approach, the amino acid sequence of BGPs as deduced from the gene is analyzed to determine regions of high immunogenicity. The corresponding polypeptides are synthesized and are used in suitable immunization protocols to raise antibodies. Analysis to select appropriate epitopes is described by, for example, Ausubel, F. M. et al, in *Current protocols in Molecular Biology,* John Wiley & Sons, Vol. 2, Sec. IV, pp11.14.1, 1989). The optimal selections are usually the C terminus, the N terminus and internal regions of the polypeptide, which are likely to be exposed to the external environment when the protein is in its natural conformation (this determination is based on the hydrophilicity of the sites). Typically, selected peptides, about 15 residues in length, are synthesized using an Applied Biosystems Peptide Synthesizer Model 431A using fmoc-chemistry and coupled to keyhole limpet hemocyanin (KLH; Sigma) by reaction with m-maleimidobenzoyl-N-hydroxysuccinimide ester (MBS) (See Ausubel et al, supra at pp 11.15.1). A cysteine is introduced at the N-terminus of the peptide to permit coupling to KLH. Rabbits are immunized with the peptide-KLH complex in complete Freund's adjuvant and the resulting antisera tested for antipeptide activity, for example, by binding the peptide to plastic, blocking with 0.1% BSA, reacting with antisera, washing and reacting with radioiodinated affinity purified specific goat antirabbit IgG.

Hybridomas may be also be prepared and screened using standard techniques. Hybrids are screened using radioiodinated BGP to identify those producing monoclonal antibody. In a typical protocol, prongs of plates (FAST, Becton-Dickinson, Palo Alto, Calif.), are coated with affinity purified specific rabbit-antimouse (or suitable anti species Ig) antibodies at 10 µg/ml. The coated prongs are blocked with 0.1% BSA, washed and exposed to supernatants from hybridomas. After incubation the prongs are exposed to radiolabeled protein, 1 ng/ml. Clones producing antibodies will bind a quantity of radioactivity which is detectable above background. Such clones are expanded and subjected to 2 cycles of cloning at 0.3 cell/well. Cloned hybridomas are injected into pristine treated mice to produce ascites, and monoclonal antibody is purified from the ascitic fluid by affinity chromatography on protein A.

F. Use of Anti-BGPs in Diagnosis

Anti-BGPs are useful for the diagnosis of prepathologic conditions and as well as chronic and acute diseases which are characterized by abnormalities in the amount or distribution of BGPs. A variety of protocols for the conduct of immunoassays, using either polyclonal or monoclonal antibodies specific for BGPs, is known in the art and include competitive binding assays and immunoradiometric assays. A two-site monoclonal-based immunoassay utilizing monoclonal antibodies reactive to two noninterfering epitopes on a specific BGP is preferred, but a competitive binding assay can also be employed. These assays are described in the following publications, hereby incorporated by reference: Maddox, D. E. et al, *J Exp Med* (1983) 158:1211; Gleich, G. J. et al, *J Lab Clin Med* (1971) 77:690; Gleich, G. J. et al, *J Allergy Clin Immun* (1974) 53:158; Gleich, G. J. et al, *J Allergy Clin Immun* (1977) 60:188; Dunnette, S. L. et al, *J Immunol* (1977) 119:1727; Wassom, D. L. et al, *J Clin Invest* (1981) 67:651.

Immunoassay procedures are utilized to measure several major parameters in immunopathologic and prepathologic conditions which are characterized by BGP abnormalities— e.g. the increased or decreased production of BGPs by basophils, the aberrant production of BGPs by cells other than basophils, and the change in intracellular or extracellular distribution of BGPs during the genesis of disease. In order to determine the normal distribution of BGP in leukocytes, peripheral blood mononuclear cells from normal individuals are prepared and analyzed as described by Ackerman et al for the localization of eosinophil granules MBP and Charcot-Leyden crystal protein to human basophils. (*J Exp Med* (1983) 158:946; *J Exp Med* (1982) 155:1597). To determine the quantity of BGPs in basophils, freeze-thawed detergent extracts of cell suspensions enriched for basophils are analyzed by immunoassay, and the slope of the binding curves are then compared to comparable binding curves generated by the purified protein.

G. Pharmaceutical Compositions

BGPs are also useful to remedy deficiencies in these proteins or to amplify immune-responses which are stimulated by these proteins. BGPs can be administered to subjects exhibiting such conditions using standard formulations such as those set forth in *Remington's Pharmaceutical Sciences*, Mack Publishing Co., Easton Pa., Latest Ed.

Thus the present invention also provides compositions containing an effective amount of compounds of the present invention, including the nontoxic addition of salts, amides and esters thereof, which may alone serve to provide the above-recited therapeutic benefits. Such compositions can also be provided together with physiologically tolerable liquid, gel or solid diluents, adjuvants and excipients.

These compounds and compositions can be administered to mammals for veterinary use, such as with domestic animals, and clinical use in humans im a manner similar to other therapeutic agents. In general, the dosage required for therapeutic efficacy will range from about 0.01 to 10,000 mcg/kg, more usually 0.1 to 1000 mcg/kg of the host body weight. Alternatively, dosages within these ranges can be administered by constant infusion over an extended period of time, usually exceeding 24 hours, until the desired therapeutic benefits have been obtained.

Typically, such compositions are prepared as injectibles, either as liquid solutions or suspensions; solid forms suitable for solution in, or suspended in, liiquid prior to injection may also be prepared. The preparation may also be emulsified. The active ingredient is often mixed with diluents or excipients which are physiologically tolerable and compatible with the active ingredient. Suitable diluents or excipients are, for example, water, saline, dextrose, glycerol, or the like, and combinations thereof. In addition, if desired, the compositions may contain minor amounts of auxiliary substances such as wetting or emulsifying agents, stablizing or pH-buffering agents, and the like.

The compositions are conventionally administered parenterally, by injection, for example, either subcutaneously or intravenously. Additional formulations which are suitable for other modes of administration include suppositories, intranasal aerosols, and in some cases, oral formulations. For suppositories, traditional binders and excipients may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders, and contian 10%–95% of active ingredient, preferably 25%– 70%.

The peptide compounds may be formulated into the compositions as neutral or salt forms. Pharmaceutically acceptable nontoxic salts include the acid addition salts (formed with the free amino groups) and which are formed with inorganic acids such as, for example, hydrochloric or phosphoric acids, or such organic acids as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The following examples are intended to illustrate but not limit the invention.

EXAMPLE 1

Preparation of Purified Human BGP

A patient with a form of chronic myelogenous leukemia (basophil leukemia with leukocyte counts over $10^5$ cells/μl and 78% basophils) underwent two treatments of cytophoresis from which $1.5 \times 10^{11}$ basophils were recovered. The basophils were purified by centrifugation over a cushion of Ficoll-Hypaque from which 95% were recovered from the interface with greater than 90% purity.

Thirty vials of basophils isolated from the patient described supra were recovered and stored at –70° C. Half of 1 vial was used to search for novel basophil granule proteins. Proteins isolated as described supra, were fractionated by reverse phase HPLC using a Brownless BU-300 C4 column. The mobile phase was 0.1% trifluoroacetic acid (TFA) containing 0–70% acetonitrile. The proteins were fractionated as described supra (FIG. 1). Approximately 25 peaks were identifiable and many of the fractions were quite heterogeneous. However, several fractions were pure enough to allow for the determination of a single amino acid sequence. The N-terminal sequences of eight such fractions are shown in Table 1.

TABLE 1

N-terminal amino acid sequences of proteins purified from basophil granule extracts. "X" represents an unidentified residue.

| Fraction No. | |
|---|---|
| 9 - | Asp—Ile—Gly—Pro—Asp—Gln—His—Thr—Ser—Arg—Pro—Trp—Gly—Gln—Thr |
| 11 - | Asp—Val—Lys—Lys—Asp—Met—Glu—Val—Ser—Cys—Pro—Asp—Gly—Tyr—Thr |
| 12 - | Val—Met—X—Pro—Asp—Ala—Arg—Ser—X—Arg—Pro—Asp—Gly—X—Thr |
| 15 - | Ala—Ile—Tyr—X—Arg—Ile—Pro—X—X—Ile—Ala—Gly—Glu—Phe—Arg—Tyr—Gly—Thr—Val—Tyr—Tyr—Gln—Gly—Ser—Leu |
| 20 - | Asp—Ile—Pro—Glu—Val—X—Val—X—Leu—Ala—Ala—Asp—Glu—Ser—Leu—Ala—Pro—Lys |
| 21 - | Lys—Pro—Pro—Gln—Phe—Thr—X—Ala—Gln—Gln—Phe—Glu—Thr—Gln—His—Ile—X—Met—Thr—X—Gln |
| 30 - | Tyr—Pro—Gln—Leu—Ala—Ile—Asn |
| 42 - | Ser—Ile—Gly—Phe—Val—Glu—Val—X—Leu—Val—Leu |

Peak 21 matches the N-terminal sequence of eosinophil-derived neurotoxin (EDN), a potent ribonuclease (41a–43). The other seven sequences are novel; these sequences were not present in the Protein Identification Resource of the National Biomedical Research Foundation, searched in August 1989.

Each of the 29 remaining vials of basophil cells contains an estimated 200 µg of extractable protein. Individual proteins recovered had yields ranging from 250 pmoles for peak 21 down to 25–50 pmoles for peaks 9 and 37 (FIG. 1). Since 25 pmoles is usually sufficient for sequencing 20 or more residues at the N-terminus, the expenditure of more vials will enable rarer species of proteins to be sequenced and will also enable more residues to be sequenced from all proteins.

What is claimed is:

1. An injectable composition, comprising:
   a pharmaceutically acceptable excipient; and
   a human basophil granule protein in an isolated and purified form, the protein having an N-terminal sequence selected from the group consisting of:
   Asp-Ile-Gly-Pro-Gln-His-Thr-Ser-Arg-Pro-Trp-Gly-Gln-Thr;
   Asp-Val-Lys-Lys-Asp-Met-Glu-Val-Ser-Cys-Pro-Asp-Gly-Tyr-Thr;
   Val-Met-X-Pro-Asp-Ala-Arg-Ser-X-Arg-Pro-Asp-Gly-X-Thr;
   Ala-Ile-Tyr-X-Arg-Ile-Pro-X-X-Ile-Ala-Gly-Glu-Phe-Arg-Tyr-Gly-Thr-Val-Tyr-Tyr-Gln-Gly-Ser-Leu;
   Asp-Ile-Pro-Glu-Val-X-Val-X-Leu-Ala-Ala-Asp-Glu-Ser-Leu-Ala-Pro-Lys;
   Tyr-Pro-Gln-Leu-Ala-Ile-Asn; and
   Ser-Ile-Gly-Phe-Val-Glu-Val-X-Leu-Val-Leu;
   wherein the N-terminal sequence is determined from Edman degradation fractions taken from human basophil granule proteins and further wherein X is an amino acid residue present at the indicated position, the human basophil granule protein being isolatable from human basophil granules.

2. A human basophil granule protein in an isolated and purified form, the protein having an N-terminal sequence selected from the group consisting of:
   Asp-Ile-Gly-Pro-Asp-Gln-His-Thr-Ser-Arg-Pro-Trp-Gly-Gln-Thr;
   Asp-Val-Lys-Lys-Asp-Met-Glu-Val-Set-Cys-Pro-Asp-Gly-Tyr-Thr;
   Val-Met-X-Pro-Asp-Ala-Arg-Ser-X-Arg-Pro-Asp-Gly-X-Thr;
   Ala-Ile-Tyr-X-Arg-Ile-Pro-X-X-Ile-Ala-Gly-Glu-Phe-Arg-Tyr-Gly-Thr-Val-Tyr-Tyr-Gln-Gly-Set-Leu;
   Asp-Ile-Pro-Glu-Val-X-Val-X-Leu-Ala-Ala-Asp-Glu-Ser-Leu-Ala-Pro-Lys;
   Tyr-Pro-Gln-Leu-Ala-Ile-Asn; and
   Ser-Ile-Gly-Phe-Val-Glu-Val-X-Leu-Val-Leu;
   wherein the N-terminal sequence is determined from Edman degradation fractions taken from human basophil granule proteins and further wherein X is an amino acid residue present at the indicated position, the human basophil granule protein being isolatable from human basophil granules.

* * * * *

UNITED STATES PATENT AND TRADEMARK OFFICE
CERTIFICATE OF CORRECTION

PATENT NO. : 5,470,825

DATED : November 28, 1995

INVENTOR(S) : Randy W. Scott, Gerald J. Gleich, and Craig G. Wilde

It is certified that error appears in the above-identified patent and that said Letters Patent is hereby corrected as shown below:

On Title page of patent, column 1, after "[73]" delete "Assignee:" and insert --Assignees:--;

on Title page of patent, column 1, after "[73] Assignee: Incyte Pharmaceuticals, Inc., Palo Alto, Calif." please add on the following line --Mayo Foundation, Rochester, Minn.--;

on Title page of patent, column 2, after "Karl Bozicevic;" please delete "Fish & Richardson" and insert --Fish & Richardson P.C.--;

col. 1, line 65, after "113:", delete "1699" and insert --1694-1702--;

col. 2, line 10, after "cells", delete "Casteils" and insert --Castells--; and

Signed and Sealed this

Fourth Day of June, 1996

Attest:

BRUCE LEHMAN

Attesting Officer

Commissioner of Patents and Trademarks